(12) United States Patent
Zang

(10) Patent No.: US 7,658,926 B2
(45) Date of Patent: Feb. 9, 2010

(54) AUTOLOGOUS T-CELL VACCINES MATERIALS AND METHODS

(75) Inventor: Jingwu Z. Zang, Missouri City, TX (US)

(73) Assignee: Opexa Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 09/952,532

(22) Filed: Sep. 14, 2001

(65) Prior Publication Data

US 2003/0091578 A1 May 15, 2003

(51) Int. Cl.
*A61K 39/38* (2006.01)
(52) U.S. Cl. .................................................. 424/184.1
(58) Field of Classification Search .............. 424/93.71; 435/372.3
See application file for complete search history.

(56) References Cited

U.S. PATENT DOCUMENTS

| | | | |
|---|---|---|---|
| 4,550,086 A | 10/1985 | Reinherz et al. |
| 4,608,365 A | 8/1986 | Engel |
| 4,677,061 A | 6/1987 | Rose et al. |
| 4,897,389 A | 1/1990 | Aroonsakul |
| 4,898,856 A | 2/1990 | Aroonsakul |
| 4,898,857 A | 2/1990 | Aroonsakul |
| 4,902,680 A | 2/1990 | Aroonsakul |
| 4,996,194 A | 2/1991 | Cohen et al. |
| 5,039,660 A | 8/1991 | Leonard et al. |
| 5,112,810 A | 5/1992 | Nagai et al. |
| 5,211,952 A | 5/1993 | Spicer et al. |
| 5,242,687 A | 9/1993 | Tykocinski |
| 5,298,396 A | 3/1994 | Kotzin et al. |
| 5,340,584 A | 8/1994 | Spicer et al. |
| 5,445,939 A | 8/1995 | Anderson |
| 5,480,895 A | 1/1996 | Friedman et al. |
| 5,494,899 A | 2/1996 | Kincade et al. |
| 5,545,716 A | 8/1996 | Johnson et al. |
| 5,552,300 A | 9/1996 | Makrides et al. |
| 5,554,595 A | 9/1996 | Kincade et al. |
| 5,569,585 A | 10/1996 | Goodwin et al. |
| 5,614,192 A | 3/1997 | Vandenbark |
| 5,643,572 A | 7/1997 | Byers et al. |
| 5,656,446 A | 8/1997 | Anderson |
| 5,668,117 A | 9/1997 | Shapiro |
| 5,674,487 A | 10/1997 | Smith et al. |
| 5,716,946 A | 2/1998 | DeLuca et al. |
| 5,723,503 A | 3/1998 | Smith et al. |
| 5,750,356 A | 5/1998 | Spack et al. |
| 5,766,920 A | 6/1998 | Babbitt et al. |
| 5,776,459 A | 7/1998 | Vandenbark |
| 5,776,708 A | 7/1998 | Kotzin et al. |
| 5,817,622 A | 10/1998 | Johnson et al. |
| 5,837,246 A | 11/1998 | Howell et al. |
| 5,843,689 A | 12/1998 | Anderson et al. |
| 5,849,886 A | 12/1998 | Määttä et al. |
| 5,858,364 A | 1/1999 | Weiner et al. |
| 5,861,164 A | 1/1999 | Howell et al. |
| 5,869,057 A | 2/1999 | Rock |
| 5,874,531 A | 2/1999 | Strominger et al. |
| 6,007,815 A | 12/1999 | Howell et al. |
| 6,033,661 A | 3/2000 | Smith et al. |
| 6,043,236 A | 3/2000 | Brattsand et al. |
| 6,054,292 A | 4/2000 | Hillman et al. |
| 6,083,503 A | 7/2000 | Lenardo |
| 6,083,521 A | 7/2000 | Acemoglu et al. |
| 6,090,387 A | 7/2000 | Howell et al. |
| 6,096,314 A | 8/2000 | Cohen et al. |
| 6,114,388 A | 9/2000 | Geffard |
| 6,130,087 A | 10/2000 | Srivastava et al. |
| 6,159,470 A | 12/2000 | Howell et al. |
| 6,187,750 B1 | 2/2001 | Chein |
| 6,207,147 B1 | 3/2001 | Hiserodt |
| 6,207,645 B1 | 3/2001 | Howell et al. |
| 6,218,132 B1 | 4/2001 | Spack et al. |
| 6,218,166 B1 | 4/2001 | Ravindranath et al. |
| 6,221,352 B1 | 4/2001 | Howell et al. |
| 6,303,314 B1 | 10/2001 | Zang |
| 6,489,299 B2 | 12/2002 | Steinman et al. |
| 6,746,670 B2 | 6/2004 | Levings et al. |
| 6,806,258 B2 * | 10/2004 | Monia ......................... 514/44 |
| 2001/0031253 A1 | 10/2001 | Gruenberg |
| 2002/0009448 A1 | 1/2002 | Weiner et al. |
| 2002/0072493 A1 | 6/2002 | Eisenbach-Schwartz et al. |

(Continued)

FOREIGN PATENT DOCUMENTS

WO    WO 91/15225    10/1991

(Continued)

OTHER PUBLICATIONS

Van Der Aa, A., et al. Cli. Exp. Immunol. 2003; 131:155-168.*

(Continued)

*Primary Examiner*—G. R Ewoldt
(74) *Attorney, Agent, or Firm*—Polsinelli Shughart PC; Teddy C. Scott, Jr.; Paul A. Jenny

(57) ABSTRACT

The present invention relates to improved autologous T cell vaccines and methods for their production. The invention is also directed to methods for treating T cell associated diseases such as multiple sclerosis are rheumatoid arthritis using autologous T cell vaccines.

12 Claims, 1 Drawing Sheet

U.S. PATENT DOCUMENTS

| | | |
|---|---|---|
| 2003/0091578 A1 | 5/2003 | Zhang |
| 2003/0153073 A1 | 8/2003 | Rogers et al. |

FOREIGN PATENT DOCUMENTS

| | | |
|---|---|---|
| WO | WO 94/26876 A1 | 11/1994 |
| WO | WO 99/13904 | 3/1999 |
| WO | WO 00/14116 | 3/2000 |
| WO | PCT/US00/22988 | 8/2000 |
| WO | PCT/US02/28874 | 9/2002 |

OTHER PUBLICATIONS

Zhang, J.Z., et al. Neurology, 2000;54(7) Suppl. 3, A23.*
Allegretta M, Nicklas JA, Sriam S, Albertini RJ (1990) T cells responsive to myelin basic protein in patients with multiple sclerosis. Science 247:718-721.
Ben-Nun A, Wekerle H, Cohen IR (1981) The rapid isolation of clonable antigen-specific T lymphocyte lines capable of mediating autoimmune encephalomylitis. Eur J Immunol 11:195-204.
Ben-Nun A, Wekerle H, Cohen IR (1981) Vaccination against autoimmune encephalomyelitis with T lymphocyte line cells reactive against myelin basic protein. Nature 292:60-61.
Chou YK, Bourdette DN, Offner H, Vandenbark AA (1992) Frequency of T cells specific for myelin basic protein and myelin proteolipid protein in blood and cerebrospinal fluid in multiple sclerosis. J Neuroimmunol 38:105-114.
Correale et al. (2000). T cell vaccination in secondary progressive multiple sclerosis. J. Neuroimmunol. 107:130-139.
European Study Group on interferon beta-1b in secondary progressive MS (1998) Placebo-controlled multicentre randomized trial of interferon beta-1b in treatment of secondary progressive multiple sclerosis. Lancet 352:1491-1497.
Genain (1995). Antibody facilitation of multiple sclerosis-like lesions in a nonhuman primate. J. Clin. Invest. 96:2966-2974.
Hafler et al. (1992). T cell vaccination in multiple sclerosis: a preliminary report. Clinical Immunol. and Immunopathology 62:307-313.
Hong et al. (1999). A common T cell receptor V-D-J sequence in V∃13.1 T cells recognizing an immunodominant peptide of myelin basic protein in multiple sclerosis. J. Immunol. 163:3530-3538.
Hong et al. (2000). Reactivity and Regulatory Properties of Human Ant-Idiotypic Antibodies Induced by T cell Vaccination. J. Immunol. 165:6858-6864.
Jacobs (1996). Intramuscular interferon beta-1a for disease progression in relapsing multiple sclerosis. Ann. Neurol. 39:285-294.
Kerlero de Rosbo et. al. (1993) Reactivity to myelin antigens in multiple sclerosis. Peripheral blood lymphocytes respond predominantly to myelin oligodendrocyte glycoprotein. J. Clin. Invest. 92: 2602-2608.
Lider (1988). Anti-idiotypïc network induced by T cell vaccination against experimental autoimmune encephalomyelitis. Science 239:181-183.
Linder et al. (1999) Brain 122: 2089.
Lohse AW, Moi F, Karin N, Cohen IR (1989) Control of experimental autoimmune encephalomyelitis by T cells responding to activated T cells. Science 244:820-822.
Markovic-Plese et al. (1995), T cell recognition of immunodominant and cryptic proteolipid protein epitopes in humans. J. Immunol. 155:982-992.
Medaer (1995). Depletion of myelin basic protein-reactive T cells by T cell vaccination: A pilot clinical trial in multiple sclerosis. Lancet 346:807-808.
Ota et al. (1990). T cell recognition of an immunodominant MBP epitope in multiple sclerosis. Nature 346:183-187.
Offner et al. (1989). Lymphocyte vaccination against experimental autoimmune encephalomyelitis: evaluation of vaccination protocols. J. Neuroimmunol. 21: 13-22.
Poser et al. (1983). New Diagnostic criteria for multiple sclerosis: Guidelines for research protocols. Ann. Neurol. 13:227-231.

Scheltens et al. (1992). White matter lesions on magnetic resonance imaging in clinically diagnosed Alzheimer's disease. Brain 115:735-748.
Selmaj et al. (1991). Identification of lymphotoxin and tumor necrosis factor in multiple sclerosis lesions.. J. Clin. Invest. 87:949-954.
Sharief MK, Hentges R (1991). Association between tumor necrosis factor-alpha and disease progression in patients with multiple sclerosis. N. Engl. J. Med. 325:467-472.
Stinissen et al. (1997). Autoimmune pathogenesis of multiple sclerosis: role of autoreactive T lymphocytes and new immunotherapeutic strategies. Crit. Rev. Immunol. 17:33-75.
The IFNB Multiple Sclerosis Study Group (1993) Interferon beta-1b is effective in relapsing-remitting multiple sclerosis. I. Clinical results of a multicenter, randomized, double-blind, placebo-controlled trial. Neurol 43:655-661.
Tejada-Simon et al. International Immunology, vol. 12, No. 12: 1641-1650.
Tejada-Simon et al. (2001) Reactivity pattern and cytokine profile of T cells primed by myelin peptides in multiple sclerosis and healthy individuals. Eur. J. Immunol. 31:907-917.
Trotter at al. (1998). T cell recognition of myelin proteolipid protein and myelin proteolipid protein peptides in the peripheral blood of multiple sclerosis and control subjects. J. Neuroimmunology 84:172-178.
Trotter et al. (1997). HPRT mutant T-cell lines from multiple sclerosis patients recognize myelin proteolipid protein peptides. J. Neuroimmunol. 75:95-103.
Truyen et al. (1990). Improved correlation of magnetic resonance imaging (MRI) with clinical status in multiple sclerosis (MS) by use of extensive standardized imaging-protocol. J. Neurol. Sci. 96:173-182.
Tuohy et al. (1999). Spontaneous regression of primary autoreactivity during chronic progression of experimental autoimmune encephalomyelitis and multiple sclerosis. J. Exp. Med. 189:1033-1042.
Vandevyver et al. (1995): Clonal expansion of myelin basic protein-reactive T cells in patients with multiple sclerosis: restricted T cell receptor V gene rearrangements and CDR3 sequence. Eur. J. Immunol. 25:958-968.
Wucherpfennig et al. (1994). Clonal expansion and persistence of human T cells specific for an immunodominant myelin basic protein peptide. J. Immunol. 152:5581-5592.
Zang et al. (2000). Th2 immune regulation induced by T cell vaccination in patients with multiple sclerosis. Eur. J. Immunol. 30:908-913.
Zang et al. (2000). Preferential recognition of TCR hypervariable regions by human anti-idiotypic T cells induced by T cell vaccination. J. Immunol. 164:4011-4017.
Zang et al. (2000). Immunoregulation and blocking antibodies induced by interferon beta treatment in MS. Neurobiology 55:397-404.
Zang et al. (2000). Aberrant T cell migration toward RANTES and MIP-1α in patients with multiple sclerosis overexpression of chemokine receptor CCR5. Brain 123:1874-1882.
Zang et al. (2001). Regulation of Chemokine Receptor CCR5 and Production of RANTES and MIP-1α by interferon-β. J. Neuroimmunol. 112:174-180.
Zhang et al. (1993). MHC-restricted depletion of human myelin basic protein-reactive T cells by T cell vaccination. Science 261:1451-1454.
Zhang and Raus (1993). T-cell vaccination in autoimmune diseases from laboratory to clinic. Human Immunol 38:87-96.
Zhang et al. (1994). Increased frequency of interleukin 2-responsive T cells specific for myelin basic protein and proteolipid protein in peripheral blood and cerebrospinal fluid of patients with multiple sclerosis. J. Exp. Med. 179:973-984.
Zhang et al. (1995). In vivo clonotypic regulation of human myelin basic protein-reactive T cells by T cell vaccination. J. Immunol. 155:5868-5877.
Zhang J., Medaer, R. Stinissen, P., Fidler, D. and Rous J. (1993). MHC-Restricted Depletion of Human Myelin Basic Protein-Reactive T Cells by T Cell Vaccination. Science 261:1451-1454.

Zhang J., Medaer R., Hashim G., Chin Y., van den Berg-Loonen E., and Raus J. (1992). Myelin Basic Protein-specific T Lymphocytes in Multiple Sclerosis and Controls: Precursor Frequency, Fine Specificity, and Cytotoxicity. Ann. of Neurology 32(3):330-338.

Minohara M., Ochi H., Matsushita S., Irie A., Nishimura Y. and Kira J. (2001). Differences between T-cell reactivities to major myelin protein-derived peptides in opticospinal and conventional forms of multiple sclerosis and healthy controls. Tissue Antigens 57:447-456.

Johnson et al. (1995) Neurol. 45 :1268.

Naparstek et al. (1983). T lymphocyte lines producing or vaccinating against autoimmune enephalomyelitis (EAE)> Functional activation induces peanut agglutinin receptors and accumulation in the brain and thymus of line cells. Eur. J. Immunol. 13 :418-423.

Zhang, J. Z., T-Cell Vaccination in Multiple Sclerosis : Immunoregulatory Mechanism and Prospects for Therapy. Crit. Rev. Immunol. 2001, vol. 21, No. 102, pp. 41-55, see entire document.

Zhang, J., et al. T cell vaccination in multiple sclerosis. Multiple Sclerosis. 1996, vol. 1., No. 6, pp. 353-356, see entire document.

Zang, Y.C.Q., et al. Th2 immune regulation induced by T cell vaccination in patients with multiple sclerosis. Eur. J. Immunol. Mar. 2000, vol. 30, No. 3, pp. 908-913, see entire document.

Zhang, J., et al., (1996) T-Cell vaccination: Clinical application in autoimmune diseases. J. Mol. Med. 74(11):653-662.

Stinissen, P., et al., (1996) Vaccination with autoreactive T-cell clones in multiple sclerosis: Overview of immunological and clinical data. J. Neurosci. Res. 45(4):500-511.

Zhang, J., et al., (2002) T-Cell vaccination in multiple sclerosis: Results of a preliminary study. J. Neurol. 249(2):212-218.

Hafler, D., et al., (1992) T-Cell vaccination in multiple sclerosis: A preliminary report. Clin. Immunol. Immunopathol. 62(3): 307-313.

Weiner L. T Cell Vaccine—A Clinical Trial for Progressive MS. National Institutes of Health Grant No. 1 R01 NS38213-01A1. Awarded Jul. 30, 1999.

Weiner L. T Cell Vaccine—A Clinical Trial for Progressive MS. National Institutes of Health Grant No. 5 R01 NS38213-02. Awarded Jul. 24, 2000.

Weiner L. T Cell Vaccine—A Clinical Trial for Progressive MS. National Institutes of Health Grant No. 5 R01 NS38213-03. Awarded Aug. 5, 2001.

Weiner L. T Cell Vaccine—A Clinical Trial for Progressive MS. National Institutes of Health Grant No. 5 R01 NS38213-04. Awarded Aug. 8, 2002.

Weiner L. T Cell Vaccine—A Clinical Trial for Progressive MS. National Institutes of Health Grant No. 2 R01 NS038213-05. Awarded Sep. 17, 2003.

Weiner L. T Cell Vaccine—A Clinical Trial for Progressive MS. National Institutes of Health Grant No. 5 R01 NS038213-06. Awarded Jul. 23, 2004.

Weiner L. T Cell Vaccine—A Clinical Trial for Progressive MS. National Institutes of Health Grant No. 5 R01 NS038213-07. Awarded Aug. 3, 2005.

Zhang, J., et al., "T-Cell Vaccination in Autoimmune Diseases," Human Immunology, vol. 38, pp. 87-96 (1993).

Zhang, J., et al., "Vaccination With Myelin-Reactive T Cells: Results of a Clinical Trial in Patients with Multiple Sclerosis," Neurology, Apr. 11, 2001, vol. 54, No. 7, Supp. 3, p. A23.

Achiron, A., "T-Cell Vaccination In Multiple Sclerosis," Autoimmunity Reviews 3, pp. 25-32 (2004).

Achiron, A., et al., "T Cell Vaccination In Multiple Sclerosis Relapsing-Remitting Nonresponders Patients," Clinical Immunology, vol. 113, pp. 155-160 (2004).

Ben-Nun, A., "The Autoimmune Reactivity to Myelin Oligodendrocyte Glycoprotein (MOG) in Multiple Sclerosis is Potentially Pathogenic: Effect of Copolymer 1 on MOG-Induced Disease," Journal Neurol., vol. 243, Suppl. 1, pp. S14-S22 (1996).

Ben-Nun, A., "The Rapid Isolation of Clonable Antigen-Specific T Lymphocyte Lines Capable of Mediating Autoimmune Encephalomyelitis," Eur. Journal Immunol., vol. 11, pp. 195-199 (1981).

Ben-Nun, A., "Vaccination Against Autoimmune Encephalomyelitis With T-Lymphocite Line Cells Reactive Against Myelin Basic Protein," Nature, vol. 292 (5818), pp. 60-61 (1981).

Hellings, N., et al., "T-Cell Vaccination in Multiple Sclerosis: Update on Clinical Application and Mode of Action," Autoimmunity Reviews 3, pp. 267-275 (2004).

Hermans, G., et al., "Cellular and Humoral Immune Responses Against Autoreactive T Cells in Multiple Sclerosis Patients After T Cell Vaccination," Journal of Autoimmunity, vol. 13, pp. 233-246 (1999).

Hermans, G., et al., "Myelin Reactive T Cells After T Cell Vaccination in Multiple Sclerosis: Cytokine Profile and Depletion by Additional Immunizations," Journal of Neuroimmunology, vol. 102, pp. 79-84 (2000).

Stinissen, P., et al., "γδ T Cell Responses to Activated T Cells in Multiple Sclerosis Patients Induced by T Cell Vaccination," Journal of Neuroimmunology, vol. 87, pp. 94-104 (1998).

Warren, K. G., et al., "Purification of Primary Antibodies of the Myelin Basic Protein Antibody Cascade From Multiple Sclerosis Patients. Immunoreactivity Studies with Homologous and Heterologous Antigens," Clin. Invest. Med., vol. 15:1, pp. 18-29 (1992).

Zhang, J., "Multiple Sclerosis: Perspectives on Autoimmune Pathology and Prospects for Therapy," Current Neurology, vol. 15, pp: 115-155 (1995).

Zhang, J., et al.,"In Vivo Clonotypic Regulation of Human Myelin Basic Protein-Reactive T Cells by T Cell Vaccination," Journal of Immunology, vol. 155, pp. 5868-5877 (1995).

Zhang, J., et al., "Myelin Basic Protein-Reactive T Cells in Multiple Sclerosis: Pathologic Relevance and Therapeutic Targeting," Cytotechnology, vol. 16, pp. 181-187 (1994).

Zhang, J., et al., T Cell Vaccination in Multiple Sclerosis: Hopes and Facts, vol. 94, pp. 112-115 (1994).

Zipp, F., et al., "Aktuelle Therapie der Multiplen Sklerose: T-Zellvakzination," Nervenarzt, vol. 65, pp. 424-425 (1994).

Zipp, F., et al., "Diversity of the Anti-T-Cell Receptor Immune Response and Its Implications for T-Cell Vaccination Therapy of Multiple Sclerosis," Brain, vol. 121, pp. 1395-1407 (1998).

Correale J, et al. Isolation and characterization of autoreactive proteolipid protein-peptide specific T-cell clones from multiple sclerosis patients. Neurology, 1995;45:1370-8.

Warren KG, et al. Anti-myelin basic protein and anti-proteolipid protein specific forms of multiple sclerosis. Ann Neurol, 1994;35:280-9.

Olsson T, et al. Autoreactive T lymphocytes in multiple sclerosis determined by antigen-induced secretion of interferon-gama. J Clin Invest, 1990;86:981-5.

Zang CQ. Preferential recognition of TCR hypervariable regions by human anti-idiotypic T cells induced by T cell vaccination. Journal of Immunology, 164:4011-7(2000).

Hohfield R. The ups and downs of multiple sclerosis therapeutics. Annals of Neurology, 49(3):281-284 (2001).

Joshi N. The T-cell response to myelin basic protein in familial multiple sclerosis: divsersity of fine specificty, restricting elements, and T-cell receptor usage. Ann Neurol, 34:385-93 (1993).

Tournier-Lasserve E. Human T-cell response to myelin basic protein in multiple sclerosis patients and healthy subjects. Journal of Neuroscience Research, 19:149-56 (1988).

Pette M. Myelin basic protein-specific T lymphocyte lines from MS patients and healthy individuals. Neurology 40:1770-6 (1990).

Liblau R. T cell response to myelin basic protein epitopes in multiple sclerosis patients and healthy subjects. Eur J Immunol, 21:1391-5 (1991).

Shanmugam A. In vivo clonal expansion of T lymphocytes specific for an immunodominant N-terminal myelin basic protein epitope in healthy individuals. Journal of Neuroimmunology, 59:165-72 (1995).

Hellings N. T-cell reactivity to multiple myelin antigens in multiple sclerosis patients and healthy controls. Journal of Neuroscience Research, 63:290-302 (2001).

Martin R. Diversity in fine specificity and T cell receptor usage of the human CD4+ cytotoxic T cell response specific for the immunodominant myelin basic protein peptide 87-106. Journal of Immunology, 148:1359-66 (1992).

Pette M. Myelin autoreactivity in multiple sclerosis: recognition of myelin basic protein in the context of HLA-DRA2 products by T lymphocytes of multiple-sclerosis patients and healthy donors. Proc Natl Acad Sci USA, 87:7968-72 (1990).

Blevins G. Future immunotherapies in multiple sclerosis. Semin Neurol, 23(2):147-58 (2003).

Feldman M. Design of effective immunotherapy for human autoimmunity. Nature, 435:612-9 (2005).

Hong J. Ex vivo detection of myelin basic protein-reactive T cells in multiple sclerosis and controls using specific TCR oligonucleotide probes. Eur J Innnnunol 34:870-81 (2004).

Martin R. Fine specificity and HLA restriction of myelin basic protein-specific cytotoxic T cell lines from multiple sclerosis patients and healthy individuals. Journal of Immunology, 145:540-8 (1990).

Hellings N. Longitudinal study of antimyelin T cell reactivity in relapsing remitting multiple sclerosis association with clinical and MRI activity. J Neuroimmunol, 126(1-2):143-60 (2002).

Sospreda M. Immunology of multiple sclerosis. Annu Rev Immunol, 23:683-747 (2005).

Martin R. Immunotherapy of multiple sclerosis: Where are we? Where should we go? Nature Immunology, 2(9)785-8 (2001).

Muraro PA. Molecular tracking of antigen-specific T cell clones in neurological immune-mediated disorders. Brain, 126:20-31 (2003).

Pender MP. A study of human T-cell lines generated from multiple sclerosis patients and controls by stimulation with peptides of myelin basic protein. Journal of Neuroimmunology, 70(1):65-74 (1996).

Lutton JD. Multiple sclerosis: etiological mechanisms and future directions. Exp Biol Med, 229:12-20 (2004).

Dornmair K. T-cell-mediated autoimmunity. Am J Pathol, 163(4): 1215-26 (2003).

Soderstrom M. T cells recognizing multiple peptides of myelin basic protein are found in blood and enriched in cerebrospinal fluid in optic neuritis and multiple sclerosis. Scand J Immunol, 37:355-68 (1993).

Kappos L. Induction of a non-encephalitogenic type 2 T helper-cell autoimmune response in multiple sclerosis after administration of an altered peptide ligand in a placebo-controlled, randomized phase II trial. Nature Medicine, 6(9): 1176-82 (2000).

Wiendl H. Therapeutic approaches in multiple sclerosis. Biodrugs, 16(3):183-200 (2002).

Bielekova B. Encephalitogenic potential of the myelin basic protein peptide (amino acids 83-99) in multiple sclerosis: results of a phase II clinical trial with an altered peptide ligand. Nature Medicine, 6(10):1167-75 (2000).

Wucherpfennig KW. Recognition of the immunodominant myelin basic protein peptide by autoantibodies and HLA-DR2-restricted T cell clones from multiple sclerosis patients. J Clin Invest, 100(5):1114-22 (1997).

Meinl E. Myelin basic protein-specific T lymphocyte repertoire in multiple sclerosis. J Clin Invest, 92:2633-43 (1993).

* cited by examiner

AUTOLOGOUS T-CELL VACCINES MATERIALS AND METHODS

BACKGROUND OF THE INVENTION

There is growing evidence suggesting that autoimmune T cell responses to myelin antigens, including myelin basic protein (MBP), are engaged in the pathogenesis of multiple sclerosis (MS) (Stinissen et al., Crit. Rev. Immunol. 1997; 17:33-75). MBP-reactive T cells are found to undergo in vivo activation and occur at high precursor frequency in the blood and cerebrospinal fluid of patients with MS (Zhang et al., *J. Exp. Med.*, 1994; 179:973-984; Chou et al., *J. Neuroimmunol.*, 1992; 38:105-114; Allegretta et al., *Science*, 1990; 247: 718-721). These MBP-reactive T cells produce pro-inflammatory Th1 cytokines (IL-2, TNF-α and γ-interferon) and are thought to facilitate myelin-destructive inflammation in the central nervous system (Sharief et al., *N. Engl. J. Med.*, 1991; 325:467-472; Selmaj et al., *J. Clin. Invest.*, 1991; 87:949-954). It has been shown that MBP-reactive T cells can induce experimental autoimmune encephalomyelitis (EAE), an animal model for MS (Ben-Nun et al., *Eur. J. Immunol.*, 1981; 11:195-204). EAE can also be prevented or cured by repeated inoculations with MBP-reactive T cells that have been inactivated by chemical treatment or irradiation, a treatment procedure termed T cell vaccination (Ben-Nun et al., *Nature*, 1981; 292:60-61). It has been demonstrated that T cell vaccination induces regulatory immune responses comprised of anti-idiotypic T cells and anti-ergotypic T cells, which contribute to the treatment effects on EAE and other experimental autoimmune disease models (Lider et al., *Science*, 1988; 239:820-822; Lohse et al., *Science*, 1989; 244: 820-822).

T cell vaccination has been advanced recently to clinical trials in patients with MS based on the hypothesis that depletion of MBP-reactive T cells may improve the clinical course of the disease. In a pilot clinical trial, we demonstrated that vaccination with irradiated autologous MBP-reactive T cell clones elicited CD8+ cytolytic T cell responses that specifically recognized and lysed MBP-reactive T cells used for vaccination (Zhang et al., *Science*, 1993; 261: 1451-1454, Medear et al., Lancet 1995: 346:807-808). Three subcutaneous inoculations with irradiated MBP-reactive T cell clones resulted in depletion of circulating MBP-reactive T cells in patients with MS. Depletion of MBP-reactive T cells by T cell vaccination appeared to correlate with clinical improvement, as evidenced by a reduction in rate of relapse, expanded disability scale score (EDSS) and MRI lesion activities in relapsing-remitting patients (Medaer et al., 1995). Although no conclusion could be made from the pilot trial due to the limited number of MS patients studied, the excellent safety profile and the potential clinical benefit encouraged further clinical investigations. This preliminary clinical trial was undertaken to investigate whether depletion of circulating MBP-reactive T cells would be clinically beneficial to patients with MS.

SUMMARY OF THE INVENTION

The present invention is directed to methods for producing autologous T cell vaccines, to the T cell vaccines produced by those methods and to methods for treating T cell associated diseases using those vaccines. One aspect of the present invention is directed to the production of autologous T cell vaccines and to the use of those vaccines for treating multiple sclerosis. Another aspect of the invention relates to the treatment of rheumatoid arthritis with T cell vaccines.

In another of its aspects, the present invention comprises an autologous T cell vaccine.

A preferred embodiment of the present invention comprises an autologous T cell vaccine prepared by a method called the direct expansion method (DEM) which provides a faster, easier and more cost effective method for preparing a T cell vaccine. The direct expansion method is the preferred method for vaccine production when T cells which have been identified as being reactive to myelin protein or fragments thereof have a stimulation index (S.I.) of 5 or higher. The direct expansion method comprises obtaining from a MS patient to be treated, peripheral blood mononuclear cells (PBMCs) or mononuclear cells from the cerebrospinal fluid of a patient (CSFMCs). The PBMCs or CSFMCs obtained from the patient are then incubated in the presence of a multiple sclerosis associated antigen such as myelin basic protein (MBP) or one or more immunogenic fragments of MBP. Other multiple sclerosis associated antigens useful in the practice of the present invention include myelin proteolipid lysoprotein, myelin oligodendrocyte glycoprotein and glatiramer, and fragments thereof. In a more preferred embodiment, the immunogenic fragment or fragments of MBP are immunodominant fragments. Most preferred MBP fragments include a fragment corresponding to amino acids 83-99 of MBP and a fragment corresponding to amino acids 151-170 of MBP. In still other embodiments of the present invention cells may be incubated without consideration of multiple sclerosis related antigens and/or fragments thereof. After incubation with MBP or fragments thereof, the PBMCs or CSFMCs are then incubated again with MBP and/or fragment thereof in the presence of antigen presenting cells (APCs). The preferred antigen presenting cells for use in the practice of the present invention include irradiated PBMCs obtained from the patient. The cells thus treated are then subjected to alternate stimulation cycles with a mitogen, preferably phytohemagglutinin and IL-2. Other mitogenic molecules useful in the process of the present invention include but are not limited to concanavalin A and poke weed mitogen. Other mitogenic molecules useful in the practice of the invention include antibodies to T cell surface receptors such as a monoclonal antibody to CD3. The alternate stimulation cycles may be repeated one or more times.

The invention is also directed to methods for treating MS using autologous T cell vaccines. The method comprises administering to a patient in need thereof, an effective dose of an autologous T cell vaccine. Preferred dosages comprise from about $40 \times 10^6$ to about $80 \times 10^6$ cells. The vaccine may be administered via any of a number of routes of administration including but not limited to intravenous, intramuscularly, intraperitoneally, intradermal, and subcutaneously. Subcutaneous injection is the preferred route of administration of the vaccine. An effective dose in the context of the present invention is the dosage necessary to result in a decrease in the number or a precursor frequency of myelin reactive T cells in the circulation of the patient. Other indicia of effective include alterations in the clinical cause of the disease as measured by widely known criteria including a decrease in EDSS or by preventing an increase in EDSS or by delay in the progression of EDSS. Other indicia of effectiveness include reduction in the rate of clinical exacerbation, or a stabilization or a reduction in the size of the brain lesions as detected by MRI or other diagnostic methodologies.

Analogously, the present invention also includes methods for treating rheumatoid arthritis using T cell vaccines prepared as described herein.

Another embodiment of the present invention provides an autologous T cell vaccine and method for producing the vaccine by the "cloning method". The cloning method is preferred when T cells which have been identified as being reactive to myelin basic protein or fragments thereof and which have a stimulation index of below 5.

The cloning method comprises identifying T cells lines reactive to MBP or myelin proteolipid lipoprotein, myelin oligodendrocyte glycoprotein, glatiramer and/or fragments of any of the foregoing as described herein. T cell lines having an S.I. of less than 5 are cloned by limiting dilution. Method comprises obtaining T cells reactive with MBP and/or fragments thereof by incubating PBMCs or CSFMCs with MBP or fragments thereof (preferably fragments corresponding to amino acids, 83-99 and to 151-170) for seven days without a change of medium. Approximately 50% from all of the wells are divided equally into two wells (antigen well and control well). Cells in both sets of wells are incubated with APCs (irradiated fresh or thawed PBMCs) in medium containing 5% v/v human $AB^+$ serum while the antigen wells receive MBP or fragments thereof as described above. The stimulation index (S.I.) is determined using a $[^3H]$ thymidine incorporation proliferation assay as described herein. Wells containing antigen and which have an S.I. of less than 5 are then cloned using limiting dilution in which cells each reactive to T cell line and pooled, diluted and seeded into wells at density of about 0.3 to about 20 cells per well in medium coating 10% human $AB^+$ serum, and an interleukin, preferably interleukin 2 along with lectin, preferably phytohemagglutinin (PHA) and with APCs. Culture medium is then changed every three to four days with medium containing IL-2. After about 14 days, the S.I. of the cells is again tested as described above. Cells are then expanded by alternate stimulation cycles with MBP (or fragments thereof) and PHA.

The present invention is also directed to an autologous T cell vaccine useful in the treatment of other T cell associated disorders such as rheumatoid arthritis. The preparation and use of such T cell vaccines is analogous to the preparation and use of the autologous T cell vaccines described above for the treatment of MS. However, the initial source of T cells is synovial fluid of rheumatoid arthritis patients. However, unlike the preparation of the vaccine for MS, the T cells derived from synovial fluid undergo stimulation by PHA; monoclonal antibody to CD3 or other mitogens and are not subjected to stimulation with antigens associated with MS.

DETAILED DESCRIPTION OF THE INVENTION

Figure 1:
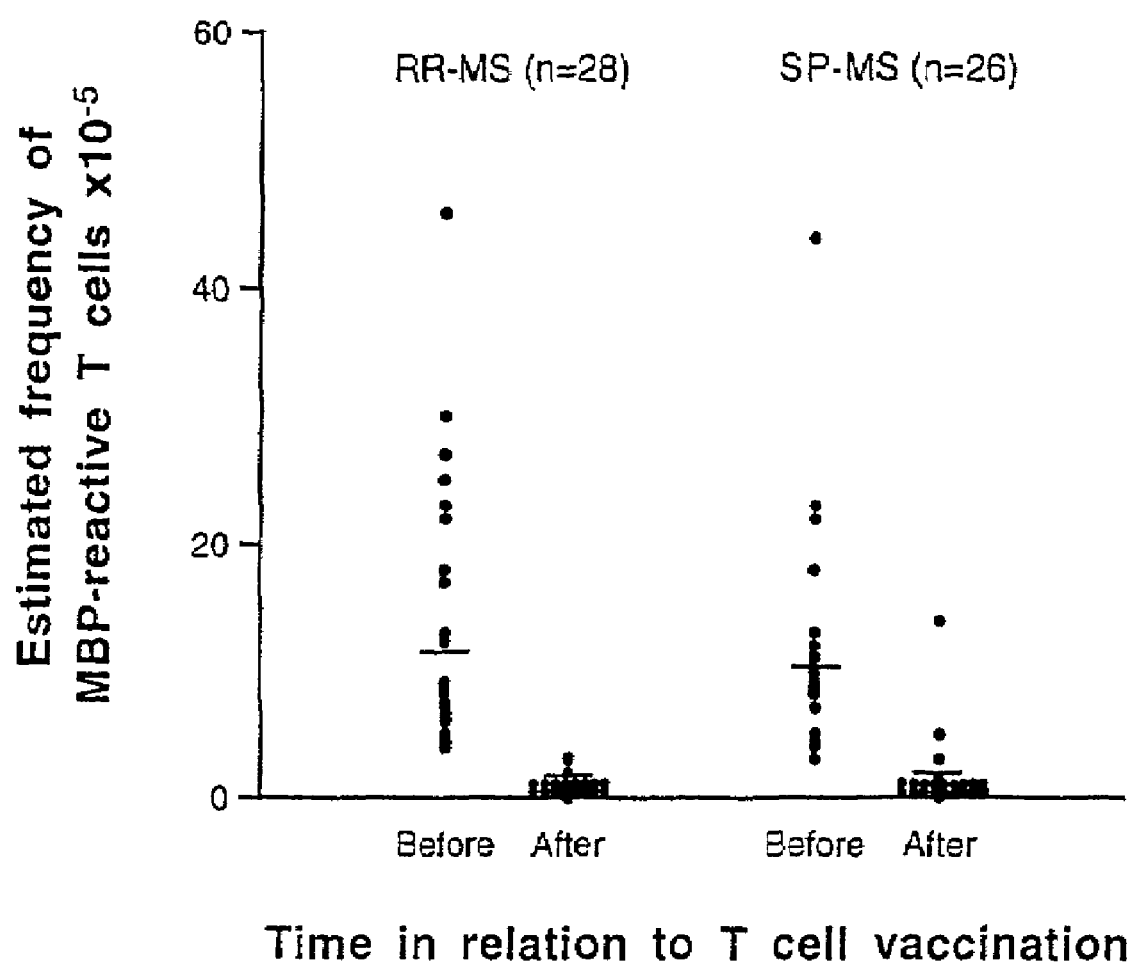
FIG. 1 illustrates the changes in the estimated precursor frequency of circulating MBP-reactive T cells before and after vaccination. Precursor frequency was estimated in all patients before and 2-3 months after completion of the vaccination protocols.

Although MBP-reactive T cells undergo in vivo activation and clonal expansion and express restricted T cell receptor V gene usage in a given individual, the T cell receptors of MBP-reactive T cells are highly diverse and vary between different MS patients (Vandevyver et al., Eur. J. Immunol., 1995; 25:958-968, Wucherpfennig et al., J. Immunol., 1994; 152:5581-5592, Hong et al., J. Immunol., 1999; 163:3530-3538). Therefore, the current strategy to effectively deplete MBP-reactive T cells in MS patients requires treatment to be individualized. The present invention provides for such individualized treatment and takes into account the diversity of T cells within an individual patient so as to provide a more effective longer lasting vaccine.

In agreement with the previous studies (Zhang et al., J. Immunol., 1993; 164:4011-4017, Medaer et al., 1995), the data herein confirms that vaccination with self MBP-reactive T cells provides a consistent and powerful means of immunizing patients to deplete circulating MBP-reactive T cells. Although the mechanism underlying immune regulation induced by T cell vaccination is not completely understood, it is increasingly clear that T cell vaccination may act on multiple regulatory networks to induce CD8+ anti-idiotypic T cell responses (Zhang et al., 1993, Zhang et al., 1995) and Th2 immune deviation (Zhang et al., 2000). In particular, these anti-idiotypic T cells induced by T cell vaccination were shown to lyse the immunizing T cells in recognition of variable regions of the T cells in recognition of variable regions of the T cell receptors, which represent the dominant immune regulation responsible for the depletion of MBP-reactive T cells (Zhang et al., 2000). It is conceivable that these regulatory responses induced by T cell vaccination potentially contribute to the beneficial effect of T cell vaccination in MS.

Although there is indirect evidence suggesting potential association of myelin-reactive T cells with the disease processes in MS (Zhang et al., 1994 Chou et al., 1992, Allegretta et al., 1990), it has been difficult to establish or reject the role of myelin-reactive T cells in the pathogenesis of MS. In this regard, T cell vaccination provides a unique opportunity to assess whether depletion of myelin-reactive T cells has a beneficial impact on the clinical course of MS.

The Examples described here describe the use of an autologous T cell vaccine prepared by a clonal selection method for the treatment of MS and an autologous T cell vaccine prepared by the direct expansion method. Data presented herein shows a favorable correlation of T cell vaccination with improved clinical variables. First, the results indicate that depletion of MBP-reactive T cells coincided with a prolonged time to progression in both relapsing-remitting and SP-MS cohorts as compared to the natural history of MS and an autologous T cell vaccine prepared by the desired expansion method. However, it should be noted that a trend for an accelerated progression was observed in some patients 12 months after the last injection. The significance of this apparent accelerated progression is unknown, but it may be associated with a gradual decline of the immunity induced initially by T cell vaccination against MBP-reactive T cells. Indeed, in approximately 10-12% of the immunized patients, MBP-reactive T cells reappeared around that time, supporting this possibility. In some cases, the reappearing MBP-reactive T cells originated from different clonal populations that were not detected before vaccination, which was also observed in the previous studies (Zhang et al., 1995). The findings suggest that MBP-reactive T cells may undergo clonal shift or epitope spreading (Touhy et al., J. Exp. Med., 1999; 189:1033) potentially associated with the on-going disease processes. This observation suggests additional booster injections may be necessary with the same or newly appearing T cell clones to maintain adequate immunity. This also suggests it may be useful to provide a T cell vaccine that is polyclonal in origin such as that provided by the direct expansion method described herein so as to avoid problems with clonal shift or epitope spreading, because the patented array of epitopes that may be recognized by such a vaccine is larger than an array recognized by a cloned population.

Annual MRI examinations of patients treated with the T cell vaccines of the present invention revealed a slight reduction in MRI lesion activities in the first year and only a 3.3% increase in the second year. The MRI findings may suggest a significant stabilization in patients treated with T cell vaccination. The MRI finding is consistent with the initial delay in time to progression that then apparently accelerated in the second year, reinforcing the possibility that the initial effect of T cell vaccination had diminished in the second year.

The methods of the present invention also resulted in favorable changes in other clinical variables, including annual rate of relapse and EDSS in vaccinated patients, suggesting a beneficial effect of T cell vaccination on the clinical course of MS. The results of the study are largely consistent with the findings reported in the pilot clinical trial (Medaer et al., 1995). However, in contrast to other clinical variables, the impact of T cell vaccination on clinical disability as measured by EDSS was minimal in both study groups. It may reflect the lack of sensitivity of the EDSS to measure changes over a relatively short period of time (24 months). The possibility also exists that even after the autoimmune component is removed or suppressed by T cell vaccination, the inflammatory lesions may still take a long time to resolve and some of the existing tissue damage will be permanent. In view of these results, the present invention provides autologous T cell vaccines for the treatment of MS as well as methods for using the vaccines for the treatment of MS.

It should be pointed out that the clinical results reported herein were compared with the patient's own pre-treatment status as well as an estimate of the natural history of MS as documented in previous MS trials and not with placebo controls. The study is also limited by the potential placebo effect associated with the open-label clinical design of the study. Therefore, although the study provided important clinical indications in favor of the role of T cell vaccination in MS, the treatment efficacy of T cell vaccination is best evaluated in double-blind and placebo-controlled clinical trials.

The present invention also provides new methods for the preparation of autologous T cell vaccines which are easier to prepare than earlier T cell vaccines and which provide a heterogeneous population of cells (non-clonal) which may act in concert to provide an improved immunological response in patients, and to avoid potential problems with epitope spreading or clonal shift, and which is designed to better eliminate a greater diversity of T cells responsible for disease.

Example 1

Estimation of the Frequency of MBP-Reactive T Cells in the Blood of MS Patients

The frequency of MBP-reactive T cells in the blood of MS patients was estimated using methods described by Zhang et al., 1994, Zhang et al., 1993, Medaer et al., 1995, (each of which is incorporated herein by reference). In each case, the material used for cell processing and cell culture was strictly autologous. Peripheral blood mononuclear cells (PBMCs) were prepared from heparinized venous blood by standard Ficoll gradient separation. The PBMCs were plated out at 200,000 cells/well (for a total of 96 wells) in RPMI 1640 (Hyclone, Logan, Utah) supplemented with 10% heat inactivated autologous serum and 50 IU/ml of recombinant interleukin-2 (IL-2), in the presence of two synthetic peptides of human myelin basic protein (MBP) corresponding to two immunodominant regions (amino acid residues 83-99 and 151-170, Tejada-Simon et al., *Eur. J. Immunol.*, 2001, March; 31(3) 907-917, respectively, at a concentration of 20 µg/ml. Incubations were carried out at 37° C. Seven days later, all cultures were restimulated with autologous pulsed irradiated PBMCs (frozen or fresh). Pulsing of PBMCs was carried out by incubating PBMCs each peptide at a concentration of 100 µg/ml at 37° C. for three hours followed by irradiation with a $^{60}CO$ source at 4,000 rads before use. After another week of incubation, each culture was examined for specific proliferation in response to the MBP peptides in proliferation assays described below.

Briefly, each well was split into four aliquots (approximately $10^4$ cells per aliquot) and cultured in duplicate with $10^5$ autologous pulsed irradiated PBMCs in the presence and the absence (controls) of the MBP peptides described above. Cultures were incubated for three days and pulsed with [$^3$H]-thymidine (Amersham, Arlington Heights, Ill.) at 1 µCi per well during the last 16 hours of culture. Cells were then harvested using an automated cell harvester and [$^3$H]-thymidine incorporation was measured in a betaplate counter. Cells were defined as reactive for the MBP peptides when the counts per minute of $^3$H-thymidine incorporated into the cells were greater than 1,500 and exceeded the counts per minute of control (in the absence of the peptides) by at least three times. The frequency of MBP-reactive T cells was then estimated by dividing the number of wells showing reactivity well by the total number of PBMCs ($19.2 \times 10^6$ cells) seeded in the initial culture (see, e.g., Zhang et al., 1994, Zhang et al., 1993, Medaer et al., 1995). The same method of calculation was used consistently to compare the changes of frequency of MBP-reactive T-cells throughout the study.

As shown in FIG. 1, the frequency of circulating MBP-reactive T-cells detected in these MS patients was approximately $14 \times 10^{-5}$ which is comparable to the frequency of about $10 \times 10^{-5}$ reported by Zhang et al., (1994), and Ota et al., *Nature*, 346:183-187 (1990) (See also Example 5).

Example 2

The Generation of Myelin-Reactive T Cells for T Cell Vaccination Preparation of PBMC and the Primary Stimulation Fresh blood specimens were processed within 2 hours of collection. Alternatively, mononuclear cells may be obtained from the cerebrospinal fluid (CSFMCs) of MS patients. Peripheral blood mononuclear cells (PBMCs) were isolated from the whole blood by standard Ficoll gradient separation method. Specifically, heparinized blood was diluted with Hanks balanced salt solution (HBSS) (1:1 blood/HBSS) and then slowly laid over the Ficoll-hypaque solution in a centrifuge tube and centrifuge for 20 minutes at 1800 rpm, 18° C. to 25° C., with no brake. PBMCs were then washed by adding excess HBSS and centrifuge at 1700 rpm for 10 minutes at 18° C. to 25° C. Purified PBMCs were washed three times in RPMI 1640 medium by centrifugation and subsequently re-suspended in AIM V medium (Gibco, Grand Island, N.Y.). Cell number was counted and cells were plated out onto 96-well U-bottomed culture plates at the concentration of 200,000 cells/well. All plates were labeled with patient number and patient initials. The myelin peptides discussed in Example 1 were added to the culture at 20 µg/ml, respectively. Plates were placed in a $CO_2$ incubator and visually inspected daily. Cells were cultured for seven (7) days without change of culture medium to selectively grow peptide-specific T cells.

Identification and Selection of MBP Peptide-Specific T Cell Lines

Approximately 50% of the cells from all wells was removed and divided equally into two wells (antigen and control wells). Either fresh or thawed PBMCs were irradiated at 8,000 (using a $^{60}Co$ source) rads and used at 100,000 cells/well as a source antigen-presenting cells (APC). Cells were cultured in RPMI 1640 containing 5% human AB+ serum. Myelin peptides described in Example 1 above were added at 20 μg/ml, respectively, to the antigen wells. Medium without myelin peptides added to the paired control wells. Alternatively, other multiple sclerosis related antigens, i.e., myelin antigens and/or fragments thereof may be used including those described by Markovic-Plese et al., *J. Immunol.*, (1995), 982-992 (proteolipid protein epitopes); Genain et al., *J. Clin. Invest.*, (1995), 2966-2974; Kerlero de Rosbo et al., *J. Clin. Invest.*, (1993) 92:2602-2608; Trotter et al., *J. Neuroimmunol.*, (1998) 84:172-178 and Trotter et al., *J. Neuroimmunol.* (1997) 75:95 (myelin proteolipid protein); Linder et al., *Brain*, (1999) 122:2089 (myelin oligodendrocyte glycoprotein); and Johnson et al., *Neurol.* (1995) 45:1264 (glatiramer [copolymer 1]). Also contemplated by the present invention is the use of combination of the foregoing antigens and/or fragments thereof.

Cells were then harvested using an automated cell harvester and [$^3$H] thymidine incorporation was measured in a Betaplate counter. The reactivity of each T cell line/well to the corresponding myelin peptide was determined by [$^3$H] thymidine incorporation proliferation assay. Specifically, cells from each well were divided into four aliquots (~$10^4$ cells per aliquot) and cultured with $10^5$ irradiated autologous PBMCs as a source of APC in the presence and absence of the myelin peptides in duplicates. Cultures were incubated for 3 days and pulsed with [$^3$H] thymidine at 1 μCi/well during the last 16 hours of the culture. A T cell line is defined as being myelin peptide-specific when both the quotient of the counts per minute (cpm) of the antigen well over cpm of control well is greater than or equal to three; and the total cpm of the antigen well is greater than 1,500. The frequency of myelin-reactive T cells was estimated according to Poisson statistics. The remaining 50% cells of identified myelin-reactive T cell lines are re-stimulated for expansion with irradiated PBMCs.

Expansion and Establishment of Selected T Cell Lines/Clones

After a T cell line was identified as being myelin peptide reactive and subsequently re-stimulated for one time, it is further propagated to produce sufficient cells for vaccination using one of the following methods: direct expansion method and T cloning method. The selection of the propagation method depends on the specificity and reactivity of the T cell lines to the myelin peptides. These properties are measured by the Stimulation Index (SI) which is calculated from results from the [$^3$H]-thymidine incorporation proliferation assay as described above. The SI is the quotient of the counts per minute (cpm) of the antigen wells cpm of the control wells. When the SI is 5 or higher, the direct expansion method is used. When the SI is below 5, the cloning method is used.

Direct Expansion Method

Briefly, myelin reactive T cells identified having an S.I. of 5 or higher, were then expanded by the direct expansion method (DEM) alternate stimulation cycles with the corresponding myelin peptides and PHA in the presence of irradiated autologous PBMCs. Each stimulation cycle was carried out for 7-10 days. More specifically, myelin reactive T cells identified as described above, cells were plated at 20,000-40,000 cells per well in the presence of irradiated PBMCs (APCs) (100,000 cells per well). Corresponding myelin peptides were added at 20 μg/ml for antigen stimulation cycle and PHA is added at 1 μg/ml for each PHA stimulation cycle, respectively. Recombinant human IL-2 was also added at 100 IU/ml on the second day of the stimulation cycle. Cultures were refreshed every three to four days with RPMI 1640 medium containing 10% human AB+ serum and 100 IU/ml rIL-2. Myelin-reactive T cells lines were propagated in alternate stimulation cycles until the total cell number reached approximately 20 million.

| T cell line | Antigen | Round of expansion | CPM Ag/control | S.I. | Cell number ($10^6$) |
|---|---|---|---|---|---|
| | Reactivity of T Cell Lines Prepared by DEM | | | | |
| 3E5 | MBP83-99 | 0 | 2,399/410 | 5.8 | 0.2 |
| | MBP83-99 | 1 | 6,991/2,021 | 3.4 | 3.4 |
| | PHA | 2 | 5,804/1,266 | 4.5 | 23.5 |
| 2C9 | MBP83-99 | 0 | 4,421/312 | 14 | 0.16 |
| | MBP83-99 | 1 | 8,220/1,882 | 4.3 | 4.2 |
| | PHA | 2 | 10,221/3,142 | 3.2 | 21.4 |

In the cloning method, T cell lines were cloned using limiting dilution assays. Cells of each myelin peptide reactive T cell line were pooled and seeded at about 0.3 to about 20 cells/well in RPMI 1640 culture medium containing 10% human AB+ serum and rIL-2 at 100 IU/mL. PHA is added at 1 μg/mL, and irradiated autologous APCs were added at 100,000 cells/well. Culture medium, RPMI 1640 containing rIL-2 at 100 IU/mL was changed every three to four days. After 14 days of culture, growth-positive wells were assayed to determine their specific reactivity to the corresponding myelin peptides as described above. Further expansion of these peptide-specific T cell lines were carried out by following the direct expansion method described above in alternate stimulation cycles with the corresponding myelin peptides and PHA.

Example 3

The Depletion of MBP-Reactive T Cells by T Cell Vaccination

Fifty-four patients with RR-MS (n=28) and SP-MS (n=26) were recruited for this open-label study. The baseline clinical characteristics of the patients are shown in Table 1. Each patient received three courses of subcutaneous injections with irradiated autologous MBP-reactive T cell clones (prepared by the cloning method) at two-month intervals prepared as described above. Patients were monitored for changes in the precursor frequency of MBP-reactive T cells, rate of relapse, EDSS and MRI lesion activities over a period of 24 months. The results were compared with pre-vaccination values in a self-paired manner. In addition, the clinical data of the placebo arms of RR-MS in the beta-interferon-1a clinical trial (Jacobs et al., 1996) and SP-MS in a recent beta-IFN-1b study (European Study Group, Lancet, 352:1491-1497 (1998)) were included to provide natural history data of MS for comparison. The baseline characteristics of the placebo control subjects described in the studies were similar to those of the patient population studied here with the exception of a lower mean EDSS.

As is shown in FIG. 1 and described briefly in Example 1, the precursor frequency of circulating MBP-reactive T cells detected in these MS patients at baseline ($14 \times 10^{-5}$) was highly comparable to that reported in previous studies (approximately $10 \times 10^{-5}$ in peripheral blood mononuclear cells) (Zhang et al., 1994, Ota et al., 1990). No significant difference was found in the precursor frequency of MBP-reactive T cells between RR-MS and SP-MS cohorts. The T cell frequency was undetectable in 92% of patients or declined substantially in the remaining patients 2-3 months after the completion of three courses of vaccination ($14\times10^{-5}$ vs. $1.9\times10^{-5}$, $p<0.0001$). The results confirmed depletion of MBP-reactive T cells by T cell vaccination in patients with MS.

Example 4

Vaccination of MS Patient Using Autologous MBP-Reactive T Cells

Fifty-four patients with MS were enrolled in this trial. The inclusion criteria were clinically definite MS for at least two years, baseline expanded disability scale score (EDSS) of 1.5 to 6.5 for RR-MS and 4.0 to 8.0 for patients with secondary progressive MS (SP-MS), and at least one exacerbation in the past two years prior to study entry for the releasing-remitting MS (RR-MS) cohort. Approximately 25% of the patients failed previously to respond to or tolerate treatment with beta-interferon or glatiramer, and the remaining patients had not been treated with these agents at least one month prior to entry and throughout the study. The patients had not taken any immunosuppressive drugs, including steroids, at least three months prior to enrolling in the study. Steroids were permitted during the study if an exacerbation occurred. Symptomatic treatments for fatigue, spasticity and bladder complaints were not prohibited. Informed consent was obtained from the patients after explaining the experimental procedures. The protocol was approved by the Institutional Human Subject Committee at Baylor College of Medicine.

The vaccination protocol was similar to that used in previous clinical studies (Zhang et al., 1993, Medaer et al., 1995). Briefly, MBP-reactive T cell clones prepared by the cloning method described above were pre-activated with phytohemagglutinin (PHA) (1 µg/ml) in the presence of irradiated PBMCs as a source of accessory cells. Cells were then cultured for 5-6 days in RPMI 1640 media supplemented with 10% heat-inactivated autologous serum and 50 units of rIL-2. Activated MBP-reactive T cells were subsequently washed three times with sterile saline to remove residual PHA and cell debris. After irradiation (8,000 rads, $^{60}$Co source), cells were resuspended in 2 ml of saline and injected subcutaneously on two arms (1 ml/arm). The number of T cells used for vaccination ranged from $40\times10^6$ to $80\times10^6$ cells per injection and was chosen by an extrapolation of T cell doses effective in experimental animals on the basis of relative skin surface areas (Ben-Nun et al., 1981). Each patient received three subcutaneous injections at two-month intervals.

Patients were then observed for time to onset of confirmed progression of disability, EDSS, rate of relapse and MRI lesion activities. The results were compared with the patient's own pre-treatment course as well as the placebo arms of two recent clinical trials in RR-MS and SP-MS patients, which served as an estimate of the natural history of MS (Jacobs et al., 1996), European Study Group, 1998). Time to progression was determined by an increase of at least 1.0 on the EDSS (Poser et al., 1983) persisting for at least 2 months. On-study exacerbations were defined by the appearance of new neurological symptoms or worsening of pre-existing neurological symptoms lasting for at least 48 hours, accompanied by objective change on neurological examination (worsening of at least 0.5 point on EDSS). Patients were instructed to report events between the scheduled regular visits, and were examined by a neurologist if symptoms suggested an exacerbation. Safety assessments included adverse events, vital signs and physical examinations at regular visits. The differences in the clinical variables in study patients before and after T cell vaccination were analyzed using the Wilcoxon's rank-sum test.

Example 5

Alteration of Clinical Course of MS after Vaccination

Attempts were made to address whether depletion of circulating MBP-reactive T cells by T cell vaccination would alter the clinical course of MS. Patients received autologous T-cell vaccinations prepared as described above. Except for mild and transient erythema at the injection site seen in some patients, no adverse effects were associated with T cell vaccination, and all patients were treated in an outpatient clinic. As shown in Table 2, the mean EDSS declined slightly in patients with RR-MS (3.21 at entry vs. 3.1 at exit) over a period of 24 months after vaccination. By comparison, there was an increase of mean EDSS by 0.61 in the natural history of RR-MS (n=56) over the same period of observation, as was reported in a trial conducted using beta-IFN-1a trial (Jacobs et al., 1996). In addition, the proportion of the patients that had either unchanged or improved EDSS was considerably higher than that of the natural MS history (75% vs. 50%). Only one patient (3.5%) in the treated RR-MS group had progressed beyond EDSS of 2.0 within 24 months as compared to 18% of patients in the natural history of MS (Table 2).

In the SP-MS cohort, mean EDSS progressed slightly (+0.12) over a period of 24 months as compared to +0.6 recorded in the natural history of SP-MS (European Study Group, Lancet 1998; 352:1491-1497). Furthermore, estimation of time to confirmed progression using the Kaplan-Meier method showed considerable delay (20% progression in 18 months for both treated groups) as compared to the natural history of MS patients (20% progression in 12 months for RR-MS and 9 months for SP-MS) (Jacobs et al., Ann. Neurol, 1996; 39:285-294, European Study Group, 1998). However, progression seemed to accelerate after 18 months (12 months after the last vaccination) in both study groups.

Example 6

Changes in Rate of Clinical Exacerbation

As shown in Table 3, annual rate of relapse declined in patients with RR-MS after T cell vaccination, representing a 40% reduction from the baseline relapse rate. No significant difference in the rate of relapse could be found between the first year and the second year of the trial. By comparison, a reduction of 25% in annual rate of relapse was observed in the natural history of RR-MS (Jacobs et al., 1996). Furthermore, the proportion of patients exhibiting no attack or fewer attacks was considerably higher than that in the natural MS history (Table 3). Although the rate of relapse decreased by 50% in SP-MS cohort, only a small number of the secondary progressive patients examined here (6/26) had relapse during the two years prior to the study entry.

Example 7

Brain Lesion Activities by Magnetic Resonance Imaging Examinations

Magnetic resonance imaging (MRI) was performed as gadolinium-enhanced T2-weighted images. Areas of higher signal intensity were scored in a semiquantitative fashion (Scheltens et al., *Brain* 1992; 115:735-748, Truyen et al., *J. Neurol. Sci.*, 1990; 96:173-182). This scoring method produced a score related to both the size and number of foci with increased signal hyperintensity. Signal hyperintensities were scored in the following regions: (i) periventricular, in the frontal and occipital region and parallel to the lateral ventricles; (ii) lobar white matter, separately in the frontal, temporal, parietal and occipital region; (iii) the basal ganglia, caudate nucleus, putamen, globus palidus and thalamus and (iv) the infratentorial region, cerebellum, mesencephalon, pons and medulla. The lesions were scored as follows: a lesion with a diameter less than 0.5 cm was given the score of '1', between 0.5 cm and 1.0 cm as '2', between 1.0 cm and 1.5 cm as '3', between 1.5 cm and 2.0 cm as '4' and greater than 2.0 cm as '5'. The confluent lesions were measured as follows: a score of '5' is given when less than 25% of the region of interest as defined above was considered to be of abnormal signal intensity, '10' and '15' for 25% and 50% when more than 50% of the visualized region of interest was affected. These values were then added to the 'individual' lesion scores.

Three gadolinium-enhanced T2-weighted MRI examinations were performed at entry (baseline), 12 months and at exit (24 months) to monitor changes in the brain lesion activities as an index of disease progression. Because of technical incompatibility of some scans performed at different medical centers, MRI scans from only 34 patients could be analyzed. All MRI scans were evaluated by an outside neuroradiologist who was not involved in the clinical trial. A semi-quantitative scoring method used previously in our pilot clinical trial and other related studies was employed to evaluate lesion activity (Medaer et al., 1995, Scheltens et al., 1992, Truyen et al., 1990). This scoring method produced a score related to both the size and number of foci with increased signal hyperintensity of T2-weighted images. As shown in Table 4, the results revealed that in 70% of the patients examined the MRI lesion scores were either unchanged or improved as defined by a reduction of at least one point in the lesion score while the remaining 30% patients had increased lesion scores during the course of the study. As a group, the changes in the mean MRI lesion score represented a 1.2% reduction in the first year and an increase of 3.3% from the baseline MRI in the second year. The changes, however, were not significant ($p>0.4$). The results may reflect stabilization or some improvement attributable to T cell vaccination since MRI lesions generally progress by approximately 10% on a yearly basis in non-treated RR-MS patients as documented in previous clinical trials (European Study Group, 1998, IFNB Multiple Sclerosis Study Group, *Neurol.*, 1993; 43:655-661). Taken together, the findings suggest a favorable correlation between the depletion of MBP-reactive T cells by T cell vaccination and clinical improvement in MS patients examined.

The invention has been described by way of non-limiting examples and by way of preferred embodiments, which are not intended to limit the scope of the invention as set out in the appended claims.

TABLE 1

Pre-treatment clinical characteristics of the patients.

| Patient group | # of cases | Mean age | Male/Female | Duration (yrs.) | EDSS at entry | Relapse rate |
|---|---|---|---|---|---|---|
| Study group | | | | | | |
| RR-MS | 28 | 45 ± 9.7 | 13/15 | 7.4 ± 7.3 | 3.2 ± 2.1 | 1.25 |
| SP-MS | 26 | 49 ± 8.1 | 10/16 | 15.5 ± 9.3 | 6.1 ± 0.9 | |
| Natural history of MS | | | | | | |
| RR-MS[a] | 143 | 36.9 ± 0.05 | 40/103 | 6.4 ± 0.5 | 2.3 ± 0.07 | 1.2 |
| SP-MS[b] | 358 | 40.9 ± 7.2 | 128/230 | 13.4 ± 7.5 | 5.2 ± 1.1 | |

[a]Placebo-control group of the beta-IFN-1a trial [7].
[b]Placebo-control group of the beta-IFN-1b trial [5].

TABLE 2

Amount of sustained change in EDSS to 2 years

| Patient group | Change | EDSS | # of cases | Percentile |
|---|---|---|---|---|
| Study group | | | | |
| RR-MS | No change | 0.0 | 15 | 53.5 |
| (n = 28) | Better | ≧0.5 | 6 | 21.4 |
| | | >1.0 | 2 | 7.1 |
| | Worse | 0.5 | 4 | 14.2 |
| | | 1.0 | 0 | 0 |
| | | 1.5 | 0 | 0 |
| | | >2.0 | 1 | 3.5 |
| | Mean EDSS change[a] | −0.11 | | |
| SP-MS | No change | 0.0 | 12 | 46.1 |
| (n = 26) | Better | ≧0.5 | 4 | 15.3 |
| | | >1.0 | 1 | 3.8 |
| | Worse | 0.5 | 5 | 19.2 |
| | | 1.0 | 1 | 3.8 |
| | | 1.5 | 1 | 3.8 |
| | | >2.0 | 2 | 7.6 |
| | Mean EDSS change | +0.12 | | |
| Natural history | | | | |
| RR-MS[b] | No change | 0.0 | 14 | 25 |
| (n = 56) | Better | ≧0.5 | 9 | 16.1 |
| | | >1.0 | 5 | 8.9 |
| | Worse | 0.5 | 11 | 19.6 |
| | | 1.0 | 4 | 7.1 |
| | | 1.5 | 2 | 3.6 |
| | | >2.0 | 10 | 17.9 |
| | Mean EDSS change | +0.61 | | |
| SP-MS[c] | Mean EDSS change | +0.60 | | |
| (n = 187) | | | | |

[a]Within-person change in EDSS from baseline to year 2.
[b]Placebo-control group of the beta-IFN-1a trial [7].
[c]Placebo-control group of the beta-IFN-1b trial [5].

TABLE 3

Frequency of clinical exacerbation

| Patient group | Annual relapse rate | # of relapse | # of patients | Percentile |
|---|---|---|---|---|
| Study group | | | | |
| RR-MS (n = 28) | 1.25 (pre-study) | | | |
| | 0.75 (24 months) | 0 | 11 | 39.2 |
| | | 1 | 4 | 14.2 |
| | | 2 | 5 | 17.8 |
| | | 3 | 5 | 17.8 |
| | | ≧4 | 3 | 10.7 |
| Natural history[a] | | | | |
| RR-MS (n = 87) | 1.2 (pre-study) | | | |
| | 0.9 (24 months) | 0 | 23 | 26 |
| | | 1 | 26 | 30 |
| | | 2 | 10 | 11 |
| | | 3 | 12 | 14 |
| | | ≧4 | 16 | 17 |

[a] Placebo-control group of the beta-IFN-1a trial [7].

TABLE 4

Mean MRI lesion score by semi-quantitative analysis and the percent change from baseline MRI.

| Patients | Baseline | 12 months (% change) | 24 months (% change) |
|---|---|---|---|
| 34 total | 14.94 | 14.76 (−1.2%) | 15.44 (+3.3%) |
| 19/34 (55%) | Unchanged | | |
| 10/34 (29%) | Increased by at least one point in MRI lesion score in 24 months | | |
| 5/34 (14%) | Decreased by at least one point in MRI lesion score in 24 months | | |

I claim:

1. An autologous T cell vaccine for the treatment of multiple sclerosis made by a process comprising:
   (a) obtaining a plurality of mononuclear cells comprising T cells from a patient to be treated with the vaccine;
   (b) incubating the T cells in the presence of a human multiple sclerosis associated antigen;
   (c) stimulating the T cells obtained in step b) with antigen presenting cells APC(s) and the multiple sclerosis associated antigen;
   (d) stimulating the T cells of step c) with the multiple sclerosis associated antigen;
   (e) stimulating the T cells of step d) with a mitogen in the presence of IL-2;
   (f) repeating steps d) and e) one or more times; and
   (g) irradiating the T cells,
wherein the multiple sclerosis antigen consists of amino acids 83-99 of myelin basic protein and amino acids 151-170 of myelin basic protein.

2. The T cell vaccine according to claim 1 wherein the plurality of mononuclear cells is obtained from the peripheral blood (PBMC) from said patient.

3. The T cell vaccine according to claim 1 wherein the plurality of mononuclear cells is obtained from the cerebrospinal fluid (CSFMC) of the patient.

4. The vaccine of claim 1 wherein IL-2 is added to the T cell in each of steps c), d), e) and f).

5. The vaccine of claim 1 wherein said APCs are irradiated PBMCs or CSFMCs obtained from the patient to be treated.

6. The vaccine of claim 1 wherein the mitogen is selected from the group consisting of phytohemagglutinin, conconavalin A, pokeweed mitogen, and monoclonal antibodies to CD3.

7. A method for preparing an autologous T cell vaccine for the treatment of multiple sclerosis made by a process comprising:
   (a) obtaining a plurality of mononuclear cells comprising T cells from a patient to be treated with the vaccine;
   (b) incubating the T cells in the presence of a human multiple sclerosis associated antigen;
   (c) stimulating the T cells obtained in step b) with antigen presenting cells APC(s) and the multiple sclerosis associated antigen;
   (d) stimulating the T cells of step c) with the multiple sclerosis associated antigen;
   (e) stimulating the T cells of step d) with a mitogen in the presence of IL-2;
   (f) repeating steps d) and e) one or more times; and
   (g) irradiating the T cells,
wherein the multiple sclerosis antigen consists of amino acids 83-99 of myelin basic protein and amino acids 151-170 of myelin basic protein.

8. The method of claim 7 wherein the plurality of mononuclear cells is obtained from the peripheral blood (PBMC) from said patient.

9. The method of claim 7 wherein the plurality of mononuclear cells is obtained from the cerebrospinal fluid (CSFMC) of the patient.

10. The method of claim 7 wherein IL-2 is added to the PBMCs in each of steps c), d), e) and f).

11. The method of claim 7 wherein said APCs are irradiated PBMCs obtained from the patient to be treated.

12. The method of claim 7 wherein the mitogen is selected from the group consisting of phytohemagglutinin, conconavalin A, pokeweed mitogen and monoclonal antibodies to CD3.

* * * * *